United States Patent [19]
Lin

[11] Patent Number: 5,925,031
[45] Date of Patent: Jul. 20, 1999

[54] TRANSPLANTATION METHOD AND CUTTING DEVICE OF A SANDWICH-TYPE TISSUE LAMINATE

[76] Inventor: Po-Kang Lin, 2F, No. 283-1, Chang Tsun Road, Taipei, Taiwan

[21] Appl. No.: 09/006,029

[22] Filed: Jan. 12, 1998

[51] Int. Cl.⁶ .................................................. A61B 17/36
[52] U.S. Cl. .............................................. 606/1; 128/898
[58] Field of Search ................................. 606/167–166, 606/168; 604/22, 20, 21

[56] References Cited

U.S. PATENT DOCUMENTS

| | | | |
|---|---|---|---|
| 5,383,874 | 1/1995 | Jackson et al. | 606/1 |
| 5,817,075 | 10/1998 | Giungo | 606/166 X |

Primary Examiner—Gary Jackson
Assistant Examiner—Vikki Trinh
Attorney, Agent, or Firm—Proskauer Rose LLP

[57] ABSTRACT

Disclosed is a transplantation method and cutting device of a sandwich-type tissue laminate. The transplantation method comprises: removing a tissue, e.g. a retina, encapsulating the removed tissue, holding and lifting a sandwich-type tissue laminate, transplanting the sandwich-type tissue laminate and suturing wound. The cutting device comprises: a body, a trephine, a power switch, a revolving member, a display, a detector and a disposable knife. By using the transplantation method and cutting device, the transplanted tissue can work normally, the operation becomes safer and more beneficial. The sandwich-type tissue transplantation can be made promptly and efficiently during the tissue transplantation operation.

8 Claims, 3 Drawing Sheets

TRANSPLANTATION METHOD AND CUTTING DEVICE OF A SANDWICH-TYPE TISSUE LAMINATE

FIELD OF THE INVENTION

This invention relates to a method of transplanting a tissue, particularly to a transplantation method and cutting device of a sandwich-type tissue laminate by which a tissue of an animal is suitably supported and protected during a transplantation operation of the tissue.

BACKGROUND OF THE INVENTION

At present, during an ophthalmologic transplantation operation of a retina from a person or an animal, such as pig, dog, rabbit, etc., or a transgenic animal, firstly an ophthalmologist removes a retina to be transplanted from an eyeball. Secondly the retina to be transplanted is placed into an carrying instrument and transferred to the inside of an eyeball of a patient or an animal. Thirdly after the retina is placed at suitable position of the patient eyeball, a wound of the eyeball is sutured in order to complete the operation. However, the retina, consisting of several layers, is very soft, fragile, delicate and easily distorted. The retina must be supported and carefully protected so as to facilitate the ophthalmologic operation. Further, a supporting protection instrument should be provided in order to carry out a lamellar whole-layer retina transplantation, a single retina layer cell/tissue transplantation, or a single retina layer cell/tissue cell simultaneous transplantation. Otherwise, the retina is easily damaged during the retina processing and transplantation, then, the retina transplantation fails.

The inventor of the present invention found the difficulties in the retina transplantation. Further, the retina can be easily damaged so that the transplanted retina can not work well. Finally, the inventor develops, with an effort, a transplantation method and cutting device of a sandwich-type retina laminate of the present invention.

SUMMARY OF THE INVENTION

It is an object of the present invention to provide a transplantation method of a sandwich-type tissue laminate by which the tissue, e.g. a retina, is supported and protected by means of two layers of biological film during the process of tissue transplantation so that the tissue is intact. The transplanted tissue can work normally, and the tissue transplantation operation becomes safer and more beneficial.

It is another object of the present invention to provide a cutting device of a sandwich-type tissue laminate comprising a trephine under constant temperature control. The trephine adheres the biological films onto the tissue, e.g. a retina, to form a sandwich-type tissue laminate, and cuts the sandwich-type tissue laminate into suitable shape so that the laminate have suitable size and shape to be consistent with those of the original tissue. The sandwich-type tissue laminate can be made promptly and efficiently during the tissue transplantation operation.

BRIEF DESCRIPTIONS OF THE DRAWINGS

DETAILED DESCRIPTIONS OF THE INVENTION

Figure 1:
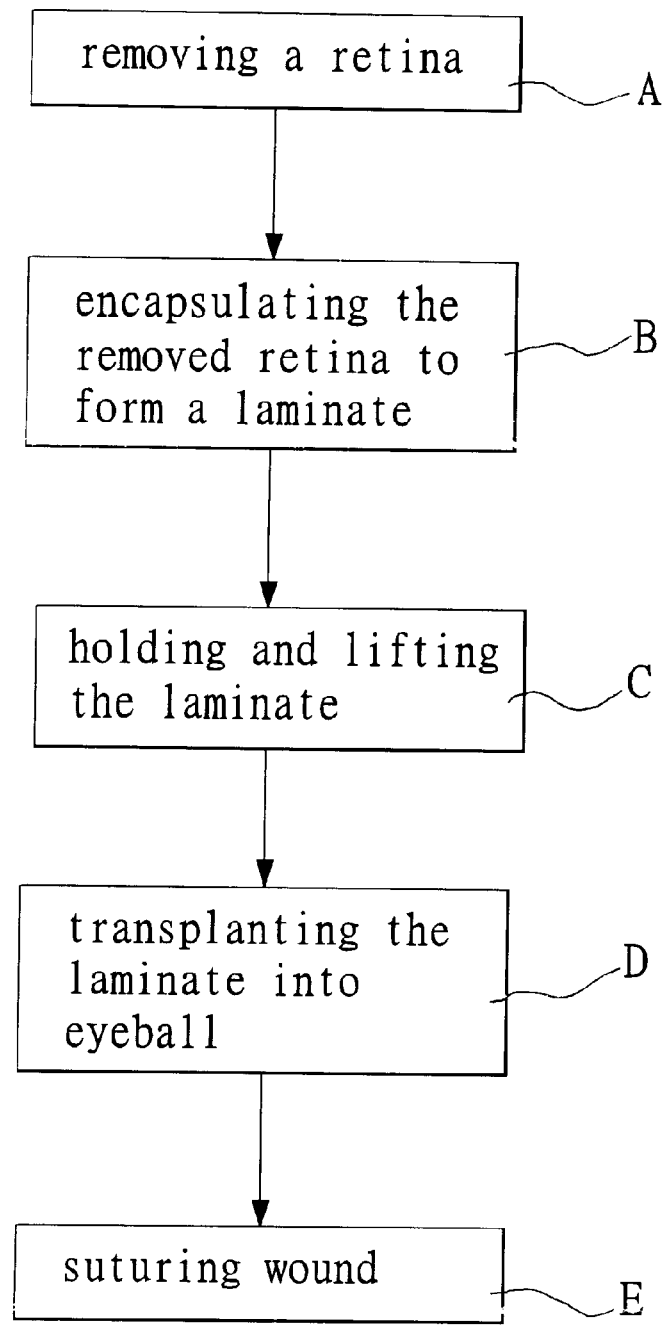
FIG. 1 is a flow diagram of the transplantation method of sandwich-type tissue laminate of the present invention.
Figure 2:
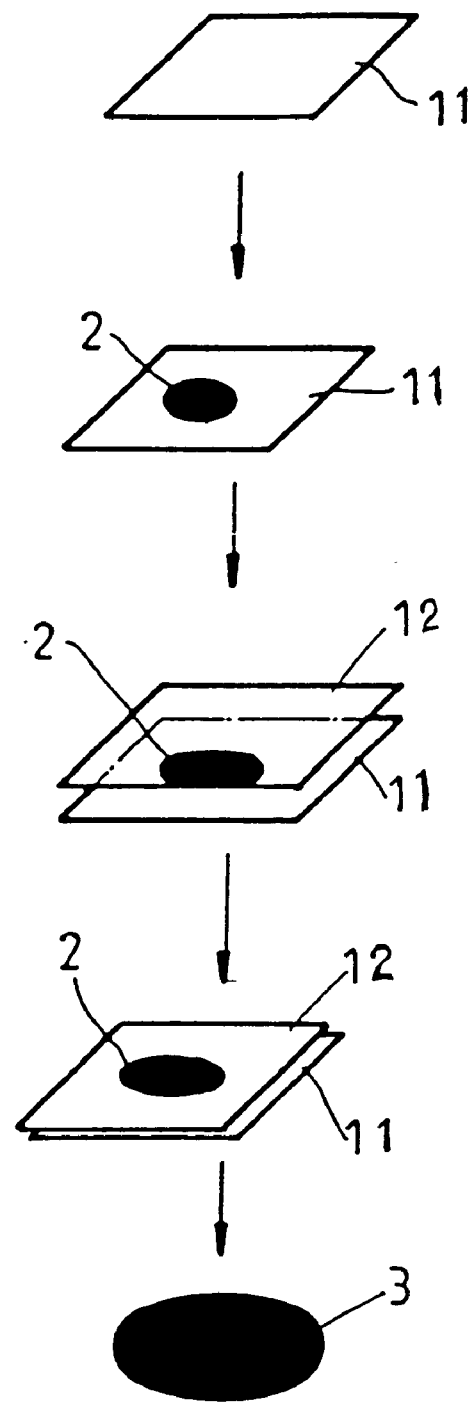
FIG. 2 is a schematic view showing the procedures of step (B) of the transplantation method of the present invention.

Please see FIG. 1 which is a flow diagram of the transplantation method of sandwich-type retina laminate of the present invention. The method comprises:

(A) removing the retina from an eyeball of a human being or animal;

(B) placing the removed retina 2 in step (A) onto a first biological film 11 as shown in FIG. 2, a small cotton bar contacting with the periphery of the retina 2 to reduce the water content of the periphery, a second biological film 12 covering the other surface of the retina 2 so that the retina 2 is encapsulated and sandwiched between the biological films 11 and 12, a cutting device of a sandwich-type retina laminate being used to adhere the first biological film 11 to the second biological film 12, the portion of the biological films 11,12 which do not contain the retina 2 being removed so that the size and shape of the biological films 11,12 are consistent with those of the retina 2 to form a sandwich-type retina laminate 3;

(C) holding and lifting the sandwich-type retina laminate 3 by means of suction or grasping;

(D) transplanting the sandwich-type retina laminate into subretinal space of the eyeball to be transplanted; and (E) suturing wound.

According to the transplantation method of sandwich-type retina laminate of the present invention, the retina is supported and protected by the biological films during the transplantation operation of the retina. The retina is not damaged so that the retina or each layer of the retina can be completely transplanted. After the operation, the transplanted retina works well.

Figure 3:
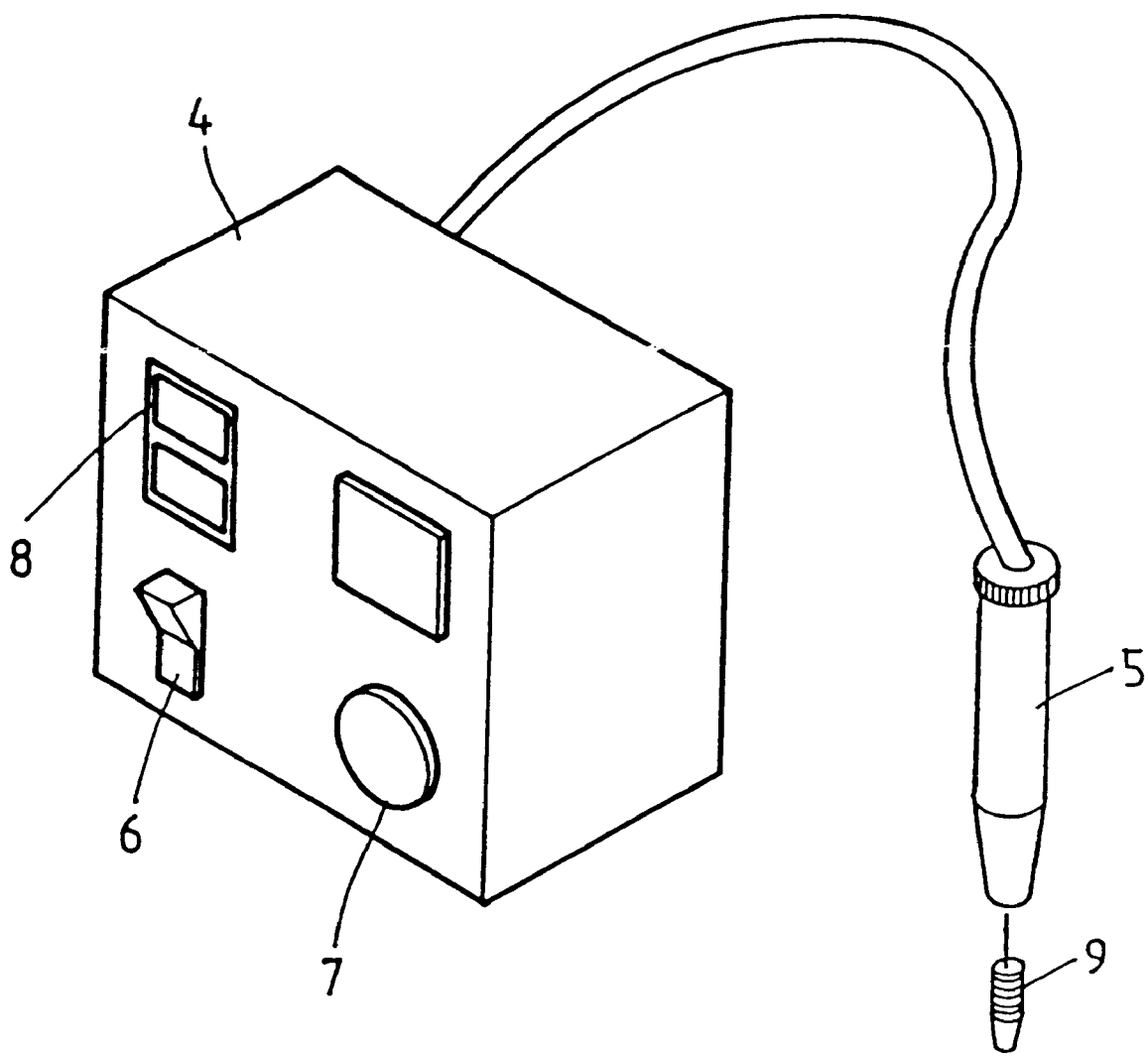
FIG. 3 is a perspective view of the cutting device of a sandwich-type tissue laminate of the present invention.

According to the present invention, the cutting device of a sandwich-type retina laminate is disclosed as shown in FIG. 3. The device comprises a body 4, a trephine 5 which is under constant temperature control and is in association with the body 4, a power switch 6 which is disposed on the body 4 and which is used to turn on or off the power, a revolving member 7 which is used to set the temperature of the trephine 5, a display 8 which is used to show the set temperature and the trephine temperature, a heating resistor (not shown) used to generate heat in the trephine 5, a detector (not shown) which is used to detect the temperature of the trephine 5, and a disposable knife 9 which is disposed at a front end of the trephine 5 and which is used to cut the sandwich-type retina laminate. The disposable knife 9 can be replaced when the knife 9 is contaminated to prevent the knife 9 from infecting the biological films 11,12 or the retina 2.

The raw materials of the biological film of the present invention are gelatin or Na-alginate. The biological film is made by homogeneously mixing the gelatin or Na-alginate with water, and casting or pouring the film on horizontal surface, such as PE sheet, glass sheet or any other flat surface, in which the swelling ratio, i.e. the changing ratio in volume before and after soaking in liquid, is below 95%. The biological film is degradable after it is put into recipient, or saline, at a temperature of 10–50° C. for one minute to several days. In other words, after the biological films sandwich the retina and are transplanted into the subretinal space of the patient eyeball, the biological film will be degraded and absorbed by the patient body so that the biological film will not adversely affect the eyeball. The raw materials of the biological film are not limited to gelatin or Na-alginate, and any other biological film made of other materials may be included in the present invention.

While the invention has been particularly shown and described with reference to these preferred embodiments, it will be understood by those skilled in the art that various changes in form and details may be made without departing form the spirit and scope of the invention. Although only the preferred embodiments of this invention were shown and described in the above description, it is requested that any modification or combination that comes within the spirit of this invention be protected.

I claim:

1. A cutting device of a sandwich-type tissue laminate comprising:

a body;

a trephine which is under temperature control and is in association with the body;

a power switch which is disposed on the body and which is used to turn on or off electrical power;

a revolving member which is used to set a temperature of the trephine;

a display which is used to show the set temperature;

a heating resistor which is used to generate heat in the trephine; and a disposable knife which is disposed at one end of the trephine and which is used to cut the sandwich-type tissue laminate.

2. A transplantation method of a sandwich-type tissue laminate comprising:

(A) removing a transplantation tissue from an original organ of a creature;

(B) encapsulating the removed transplantation tissue by sandwiching the transplantation tissue with two layers of biological film to form a sandwich-type tissue laminate;

(C) holding and lifting the sandwich-type tissue laminate by suction;

(D) transplanting the sandwich-type tissue laminate into an inner space of a patient organ to be transplanted; and (E) suturing wound.

3. The transplantation method of a sandwich-type tissue laminate as claimed in claim 2, wherein the transplantation tissue is retina.

4. The transplantation method of a sandwich-type tissue laminate as claimed in claim 3, wherein the sandwich-type tissue laminate is a sandwich-type retina laminate.

5. The transplantation method of a sandwich-type tissue laminate as claimed in claim 3, wherein the step (B) of encapsulating the removed retina comprises placing the removed retina onto a first biological film, contacting periphery of the retina with a small cotton bar to reduce water content of the periphery, covering the other surface of the retina with a second biological film, adhering the first biological film to the second biological film by using the cutting device of claim 1, and removing a portion of the biological films which do not contain the removed retina by using the cutting device of claim 1.

6. The transplantation method of a sandwich-type tissue laminate as claimed in claim 2, wherein the original organ is an eyeball.

7. The transplantation method of a sandwich-type tissue laminate as claimed in claim 2, wherein the patient organ is an eyeball.

8. The transplantation method of a sandwich-type tissue laminate as claimed in claim 2, wherein the holding and lifting of the sandwich-type retina laminate is done by grasping.

* * * * *